(12) United States Patent
Cole (10) Patent No.: US 7,485,863 B2
(45) Date of Patent: Feb. 3, 2009

(54) METHOD AND APPARATUS FOR INVESTIGATING A SAMPLE

(75) Inventor: Bryan E. Cole, Cambridge (GB)

(73) Assignee: TeraView Limited, Cambridge (GB)

( * ) Notice: Subject to any disclaimer, the term of this patent is extended or adjusted under 35 U.S.C. 154(b) by 110 days.

(21) Appl. No.: 10/568,949

(22) PCT Filed: Aug. 20, 2004

(86) PCT No.: PCT/GB2004/003626

§ 371 (c)(1),
(2), (4) Date: Aug. 31, 2006

(87) PCT Pub. No.: WO2005/019807

PCT Pub. Date: Mar. 3, 2005

(65) Prior Publication Data

US 2007/0138392 A1    Jun. 21, 2007

(30) Foreign Application Priority Data

Aug. 22, 2003 (GB) ................................ 0319840.5

(51) Int. Cl.
*G01N 21/35* (2006.01)
(52) U.S. Cl. .................................. 250/341.1

(58) Field of Classification Search ............... 250/341.1
See application file for complete search history.

(56) References Cited

U.S. PATENT DOCUMENTS

| | | | |
|---|---|---|---|
| 4,197,457 A | | 4/1980 | Cheo |
| 5,623,145 A | * | 4/1997 | Nuss .......................... 250/330 |
| 5,813,987 A | | 9/1998 | Modell et al. |

FOREIGN PATENT DOCUMENTS

| | | |
|---|---|---|
| EP | 0 468 817 A3 | 1/1992 |
| EP | 0 727 671 A2 | 8/1996 |
| EP | 0 841 548 A2 | 5/1998 |
| GB | 1 367 636 | 9/1974 |
| GB | 2 385 415 A | 8/2003 |
| WO | WO 00/75641 A1 | 12/2000 |
| WO | WO 01/48457 A1 | 7/2001 |

* cited by examiner

*Primary Examiner*—Constantine Hannaher
(74) *Attorney, Agent, or Firm*—Dickstein Shapiro LLP (57) ABSTRACT

Method and apparatus for irradiating a sample with Terhertz radiation and detecting non-specular radiation in order to characterise the internal structure of the sample. Terahertz radiation specularly reflected from the surface is minimised so that it does not mask the weaker signal originating from the internal structure of the sample.

22 Claims, 6 Drawing Sheets

METHOD AND APPARATUS FOR INVESTIGATING A SAMPLE

The present invention relates generally to the field of apparatus and methods for investigating a sample, such as to obtain information about the composition of the sample. More specifically, the present invention relates to analysing a pharmaceutical sample and obtaining information about the composition of the sample using radiation in the infra-red (IR) and Terahertz frequency range in the range from 25 GHz to 100 THz. However, in this type of imaging technology, all such radiation is colloquially referred to as THz radiation, particularly that in the range from 25 GHz to 100 THz, more particularly that in the range of 50 GHz to 84 THz, especially that in the range from 100 GHz to 50 THz.

There are various fields where it is desirable to characterise the internal structure or texture of an object. One example is pharmaceutical tablets.

The production of pharmaceuticals is a costly and complex procedure. In general the procedure involves four key stages, namely:

Drug Discovery
Product Development
Process Development for manufacturing the product; and
Manufacture One aspect of drug discovery involves identifying polymorphs and their salts that may be pharmaceutically active. This involves a high throughput polymorph detection and screening process. Possible pharmaceutical candidates are identified in this screening, and these candidates then progress to the product development stage, where they undergo clinical trials. In the clinical trials one or more active components are combined with certain inert excipients, such as lactose and sucrose. The structure and distribution uniformity of the active ingredient(s) in the combined form is then assessed. For example, the composition is assessed in terms of how it is compressed and bound together in a dosage form. Various excipients can be trialled at this stage until the most suitable excipients are determined. Hence at this stage it is desirable to be able to image the chemical composition. It would be particularly desirable to obtain a three dimensional image in a short period of time and with a high throughput.

The process development stage evaluates how to process the one or more active components with the excipients on the production line. For example, where the active component is being formed into tablets, a suitable process needs to be developed for blending and compressing the components in a tablet press. This is a critical step in pharmaceutical development, as seemingly simple formulations with identical ingredients can perform radically differently depending upon how the ingredients are blended together. For example, it is not uncommon for active ingredients in a dosage form to be unevenly distributed and in clumps, particularly where the dosage concentration is low. This is undesirable, as the therapeutic value of the tablet often depends on the distribution of the active ingredient. This problem is compounded with pharmaceuticals containing highly active ingredients and also with those that are administered by complex delivery systems. Therefore, granularity and density are important parameters of pharmaceutical tablets.

The final phase of the pharmaceutical development procedure is the manufacturing stage. At this stage it is desirable to monitor the composition of the products being manufactured in order maintain quality standards.

Therefore, at all of these stages in the pharmaceutical development process there is a need to be able to obtain information about the composition of a pharmaceutical product. There is also a need to be able to image the pharmaceutical product and obtain a three dimensional image of the composition of the product.

There is also a need for investigating pharmaceutical products, particularly highly toxic or reactive ones, in a non-invasive, efficient manner and with minimal contact.

Known techniques of assessing pharmaceutical compositions include performing tablet assays, which entail invasive sample preparation procedures such as tablet crushing, dissolution and chromatographic separation of active ingredients from excipients. These techniques are of limited value, however, as all the information on the physical state of the ingredients and how they relate to each other is effectively lost due to their invasive nature. In this regard, the quality of a formulation can be assessed via the structure of the matrix that evolves during the manufacturing process. Therefore it is desirable to have a non-destructive technique that can characterise the granularity and density of the pharmaceutical tablet, and still maintain the matrix structure.

A technique that has been used to assess tablet content uniformity involves staining the sample to generate image contrast between active ingredients and excipients. While this technique maintains the matrix structure, the staining process is invasive.

NIR spectroscopy has been used to image pharmaceuticals, as described in the article entitled "A near infrared view of pharmaceutical formulation analysis" by Lewis, Carroll and Clarke published in NIR News Vol. 12, No. 3 (2001). The technique however, is not able to readily provide an indication of how the active ingredients are heterogeneously distributed throughout the tablet, as only an image of the surface can be obtained.

Another approach uses Raman spectroscopy. This technique obtains Raman image data and applies multi-variant image processing thereto. This can provides a surface map indicating spatial distribution of ingredients. It is generally a better technique than NIR contrast enhancement approaches in that it is able to map active and excipient materials even when both are white powders. However, once again, only an image of the surface of the tablet can be obtained.

Therefore, both NIR and Raman spectroscopy are able to provide images identifying chemical specificity, but due to issues of scattering, they are not able to probe much below the surface of the sample.

Another problem with Raman spectroscopy is that it cannot be used on chemicals that fluoresce, as this masks the Raman signal. Further, high power illumination is a feature of Raman spectroscopy, and this can lead to heating and changes in chemistry of the sample being analysed.

Micro-computed tomography and magnetic resonance imaging are able to internally investigate a sample, but these techniques require long periods of time to produce an image. Furthermore, the contrast mechanisms of these techniques are limited to specific types of contrast. For example, X-ray CT techniques are sensitive only to atomic density, while MRI is sensitive to a small number of atomic species such as hydrogen or phosphorous. Neither technique is directly sensitive to the molecular structure of the material.

Terahertz radiation has been used to internally image a sample, such as is described in EP 0 727 671. This technique, however, concentrates on analysing specularly reflected radiation so as to image interfaces in a sample due to a change of refractive index.

In one aspect the present invention provides a method of investigating a sample comprising:

irradiating the sample with radiation having at least one frequency in the range from 25 GHz to 100 THz;

detecting radiation that is scattered by the sample using a detector positioned relative to the sample so as to reduce detection of specular radiation.

Preferably the detected radiation is substantially only non-specular radiation. It is also preferable that the radiation detected is back-scattered radiation.

Non-specular radiation is radiation scattered off internal structural features of the sample, such as features due to granularity, density distribution, impurities and cavities in the sample. Such scattering occurs over a wide range of angles when the size of the features are comparable or smaller than the THz wavelength. Therefore by detecting non-specular Terahertz radiation it is possible to attain information indicative of these internal features of the sample.

Ideally this detection should be undertaken so as to exclude or at least minimise specular THz radiation, particularly specular radiation reflected off the sample surface. This is because when THz radiation is incident on a surface, a large proportion is specularly reflected off the surface of the sample, and therefore tends to mask the weaker non-specular signals. Further, since the THz specular reflections predominantly originate from the surface of the sample they are not indicative of internal sample features. Therefore, by positioning a receiver out of the angular range to be expected by Snell's law for reflected radiation off the sample surface, it is possible to obtain a clearer non-specular signal.

Preferably the level of radiation detected has been scattered in a non-specular manner is higher than the level of any other radiation which may be detected.

Generally the level of specular radiation reflected/transmitted by a sample is greater than the level of non-specular radiation, so it is desirable to minimize the degree to which specular radiation is detected, in order for a clearer non-specular signal, indicative of internal sample features, to be obtained. The amount of surface specular radiation detected should be minimal, so that the non-specular radiation signal detected is more: significant and not masked by this specular radiation.

Preferably no surface specular radiation is detected. This may be achieved by positioning the detector out of the surface specular reflection path. Alternatively, the sample may be positioned so as to direct surface specular reflection away from the detector or detectors.

Preferably the detected radiation is analysed to determine a characteristic of the sample. Preferably the analysis involves:
  obtaining a time domain waveform from the detected radiation;
  obtaining a frequency spectrum from the time domain waveform;
  deriving information characterising the sample from the frequency spectrum.

The information derived characterises an internal structure of the sample. For instance, the information derived may characterise the granularity and/or density of the sample, or impurities or defects in the sample. Further, three dimensional distribution information may be derived which characterises the sample. In this regard, the information derived may be used to image the sample.

This analysis may be undertaken by irradiating a large area of the sample surface, relative to the irradiation wavelength, or by raster scanning, so as to irradiate the sample at a number of points on the sample surface to obtain information characterising the whole sample or a region of the sample.

According to a further aspect, the present invention provides an apparatus for investigating a sample comprising:
  emitter for irradiating the sample with radiation having a frequency in the range from 25 GHz to 100 THz;
  detector positioned relative to the sample so as to reduce detection of specular radiation.

Preferably the detector is positioned relative to the emitter so as to detect substantially non-specular radiation.

The apparatus may comprise one or more additional detectors for detecting non-specular radiation scattered by the sample. The detector or detectors should also preferably be configured so as to maximise the detection of scattered non-specular radiation. Since non-specular radiation is scattered over a large regions, the detector or detectors are preferably configured to detect radiation over as large a region as possible, but not encompassing the region over which specular radiation is reflected.

In this regard, it is preferable that the emitter is positioned so as to irradiate the sample over a first region, which radiation is specularly reflected by the sample over a second region and the detector is positioned so as to receive radiation scattered by the sample over a third region, such that the third region is different to both the first region and the second region.

Further, it is preferable that the third region does not overlap with the first and second regions.

Where the emitter is configured to direct radiation at a normal direction to the sample surface, the first region will be the same as the second region. Where the emitter us configured to direct radiation at close to (but not exactly) a normal direction to the sample surface, there may be a region of overlap between the first and second regions.

The apparatus may also comprise one or more additional emitters, for example, in order to increase illumination of the sample or illuminated area. In this arrangement, all of the detectors used for detecting non-specular radiation are positioned to substantially avoid the specularly reflected radiation originating from all emitters.

In addition to at least one detector positioned relative to the sample so as to reduce detection of specular radiation, the apparatus may comprise a detector for detecting specular radiation.

It is to be appreciated that throughout this specification, the term non-specular reflection will be used in relation to any radiation incident on a material that is scattered off due to variations in the material. The scattering may be back-scattering and/or forward-scattering. In other words, non-specular reflection covers all scattered radiation, but not radiation reflected directly off the surface of the material, which is generally the largest source of reflected radiation.

These aspects of the invention are particularly useful in characterising a pharmaceutical sample.

Therefore the present invention combines the use of Terahertz irradiation, which allows internal feature information to be obtained from an object, and the detection of non-specular radiation, in order to obtain a more accurate representation of the internal characteristics of the object.

The present invention will now be described with reference to the accompanying Figures, in which.

Figure 1:
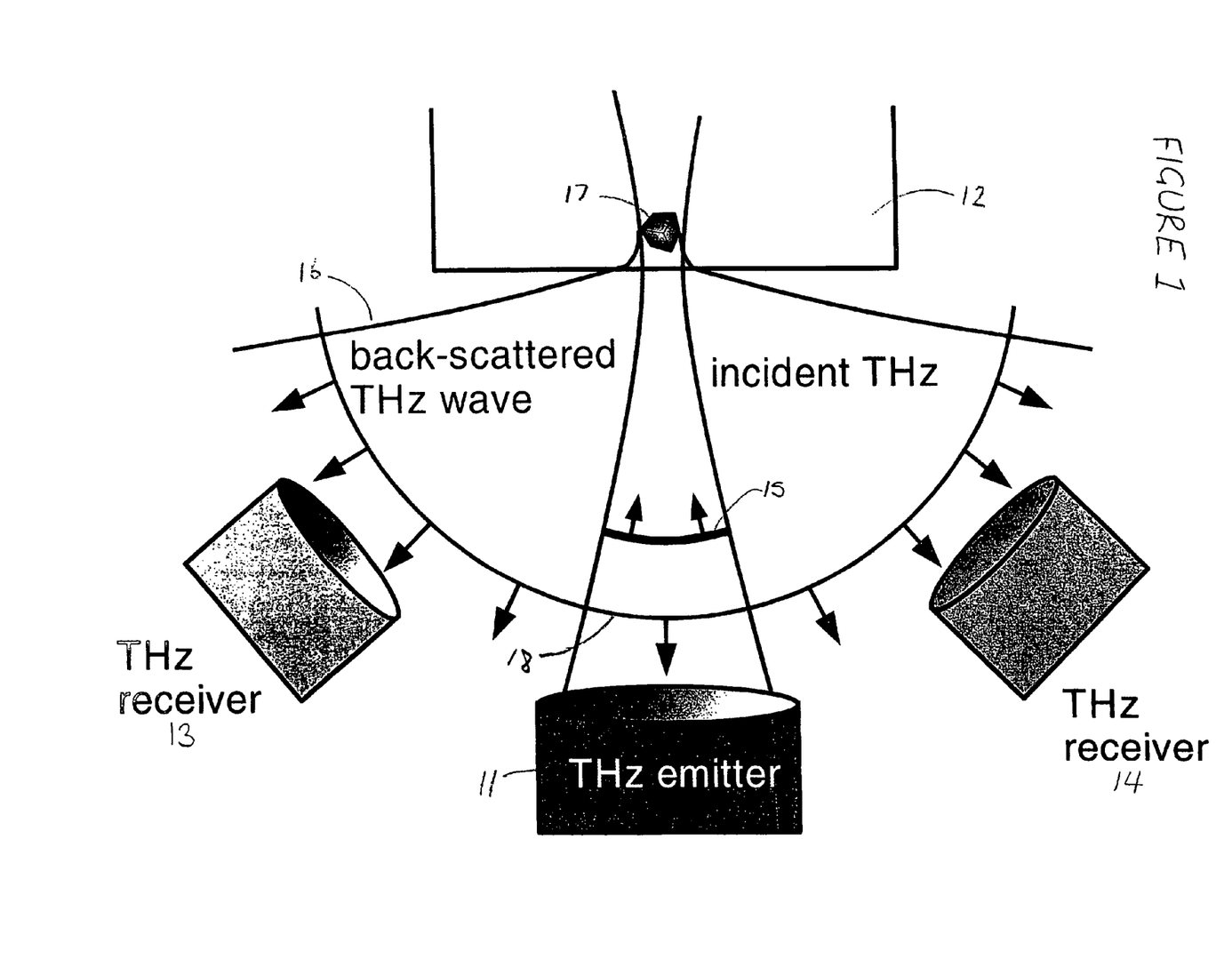
FIG. 1 depicts a THz generation/detection system according to an embodiment of the invention illustrating the operation of the system in relation to an impurity of a sample.

With reference to FIG. 1, an arrangement for measuring non-specular radiation is schematically illustrated. The arrangement comprises a THz emitter positioned adjacent a surface of a sample 12, which in this instance is a tablet sample. In this embodiment, the emitter 11 is configured to irradiate a point on the sample, although in other embodiments, a wider area could be irradiated.

The THz emitter can be positioned at any angle to the sample, but it is preferably positioned so that the primary direction of the emitted radiation is normal to the surface of the sample. Where radiation from the emitter is emitted about a range of angles, the primary direction refers to a central axial direction of the emitted radiation. In FIG. 1 the primary direction of the emitted radiation is normal to the sample surface.

A first THz receiver 13 and a second THz receiver 14 are positioned adjacent the surface of the sample 12 so as to receive non-specular radiation. More specifically, the receivers 13 and 14 are positioned so as to measure back-scattered non-specular radiation. Preferably the receivers 13 and 14 are positioned so as to maximise the collection of the back-scattered THz while simultaneously minimising collection of the specular THz.

In this regard, the funnel 15 is representative of the emitted radiation's wave path from the emitter 11 towards the sample 12. The radiation is focussed to a point on the sample by a lens (not shown).

At this point on the surface, much of the incident radiation will be specularly reflected 18 off the surface. Since the primary direction of the incident radiation is normal to the sample surface, this specular radiation 18 will be reflected back towards the emitter 11, in the same wave path 15 as the incident radiation, only the reverse direction.

The incident radiation that is not specularly reflected from the surface will proceed into the sample 12. As shown in FIG. 1, the sample includes an impurity 17. The radiation incident on this impurity is scattered off this impurity 17 in various directions. This is called non-specular reflection and can be forward scattered or back scattered. The radiation that is back-scattered, or in other words back reflected, is indicated by the arc 16. Considered from the focal point on the surface of the sample this arc can cover the following range of angles:

$$0 < arc < 180°$$

The THz radiation will be scattered in a non-specular manner due to variations in the sample material, such as due to impurities in the sample, refractive index variations and/or differences in absorption characteristics. The refractive index for THz radiation and the absorption of THz are dependent upon the local density of the material and also the material's chemical composition.

Defects of size comparable or smaller than the THz wavelengths utilised will act as scattering centres. A defect can comprise any local change in composition of the material under test, including chemical or structural changes. Therefore, a small granular impurity embedded in an otherwise pure tablet could be detected and, if required, visualised. The emitter/receiver configuration as shown in FIG. 1 is configured to allow these determinations.

It is to be appreciated that throughout this specification, the term non-specular reflection will be used in relation to any radiation incident on a material that is scattered off due to variations in the material. The scattering may be back-scattering and/or forward-scattering. In other words, non-specular reflection covers all scattered radiation, but not radiation reflected directly off the surface of the material, which is generally the largest source of reflected radiation.

In this regard, standard reflection detection systems are configured to collect the maximum back-reflected specular THz radiation possible. Under normal conditions the largest source of reflected THz radiation originates from the outer surface of the tablet or other object under test, which occurs in the region of the THz entry point into the object. The strength of this surface-reflected THz tends to mask the weaker signals originating from the internal structure of the tablet.

The FIG. 1 embodiment therefore differs from this standard arrangement, in that it is configured to measure back-scattered radiation rather than back-reflected radiation. Preferably the THz receivers 13 and 14 in FIG. 1 are configured so that they totally exclude the THz radiation specularly reflected from the sample's surface. This allows the receivers to instead detect the weaker internally scattered signals more clearly. In other words, by removing the specularly reflected THz from the THz detection system, the THz signal due to scattering from small defects may be isolated.

This apparatus of FIG. 1 can be used to determine whether or not a sample has impurities. In this regard, the FIG. 1 example illustrates how receivers 13 and 14 can be arranged to receive non-specular radiation. Preferably the THz receivers 13 and 14 detect scattered radiation over a wide region covering a wide range of detection angles, so that the detected signal is stronger.

Figure 2:
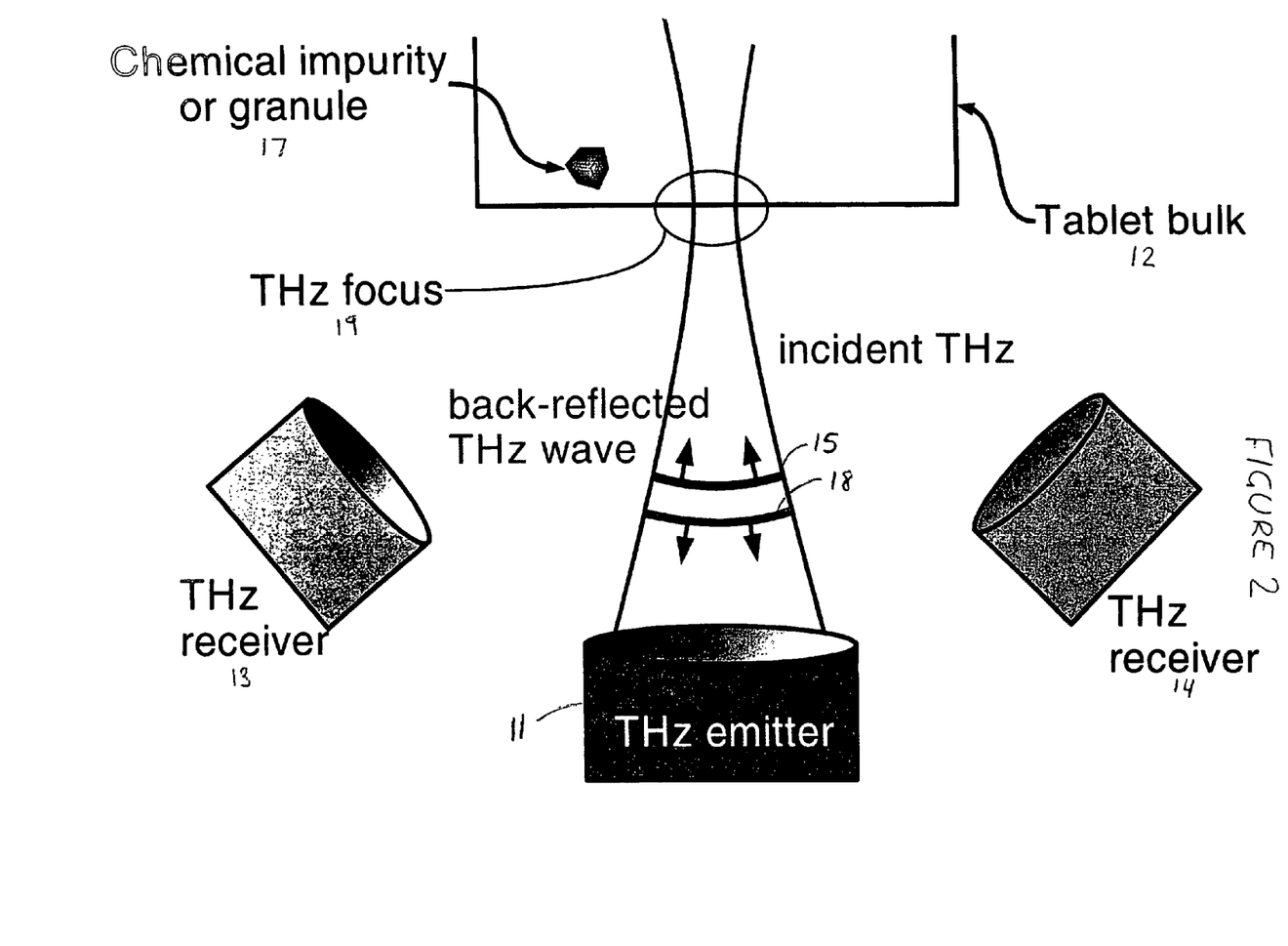
FIG. 2 depicts the operation of the THz generation/detection system of FIG. 1 in relation to a homogeneous portion of the sample.

FIG. 2, illustrates the same apparatus, where the emitted radiation 15 is incident on a homogeneous volume of the sample, in that the volume does not contain any impurities. As before, at the focal point 19 on the surface of the sample, much of the incident radiation is specularly reflected 18 off the surface and reflected back towards the emitter 11. The remainder of the incident THz radiation does not encounter any impurities or granularities in the sample volume and therefore is transmitted through the sample without scattering. Therefore the receivers 13 and 14 do not detect any non-specular radiation in this instance, which indicates that the sample is homogeneous. Hence this embodiment of the invention may be used to detect defects in nominally homogeneous materials, such as pharmaceutical tablets, to determine whether any impurities are in the tablets.

To acquire an image of the sample or a part of the sample, the THz focus is raster scanned across the tablet surface, and the sample irradiated at a plurality of points. The THz receivers 13 and 14 record any received THz signal for each of the points. Either the emitter/detector apparatus may be moved in the raster scanning, and/or the sample itself.

Although FIGS. 1 and 2 show two THz receivers 13 and 14, in another embodiment of the invention, only one THz receiver need be used. It is however preferable to have more than one THz receiver, as multiple receivers increase the overall signal-to-noise performance of the system.

Other applications of the FIG. 1 apparatus include investigating non-homogeneous samples to determine characteristics of the samples and also imaging the samples to show the characteristics visually.

In this regard, the scattering spectrum of an inhomogeneous material is a detailed function of the material's structure. Where a large area of the sample material is irradiated, the scattering spectrum will be a function of the statistical average of scattering potential presented by the material. The refractive index and absorption coefficient distribution together make up the material scattering potential. The scattering potential is also a function of position in the sample and also of THz frequency (since the material may have a frequency dependent refractive index and absorption). One other common source of scattering potential is the density distribution of the material, which is inherent in any granular material. Therefore, where THz radiation is applied to a material, low-density regions or cavities in the material are equivalent to regions of reduced refractive index.

Figure 7:
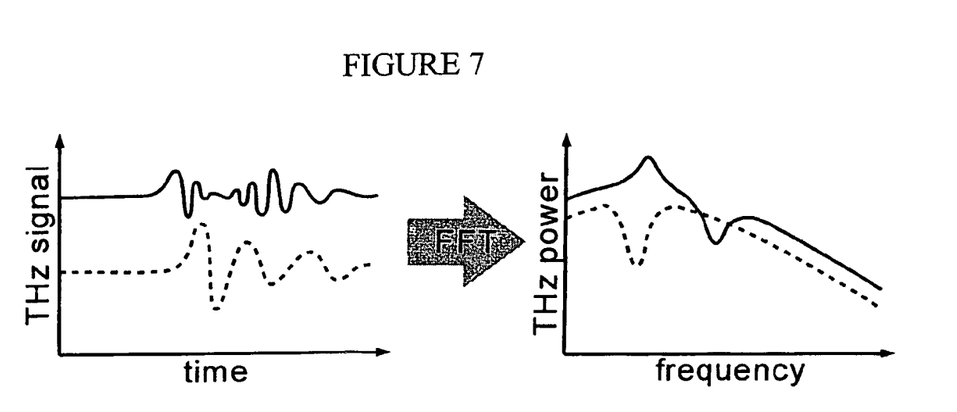
FIG. 7 compares illustrates data measured as a function of time (left) and corresponding frequency spectra (right).

The THz receivers 13 and 14 detect non-specular radiation in the same manner as known THz detectors detect specular radiation, and will not be further described herein. The raw data takes the form of a signal voltage measured as a function of optical delay (i.e. time). This is shown conceptually in the first graph in FIG. 7. Preferably this time domain waveform is converted to a frequency domain THz power spectrum by Fourier transform, as shown in the second graph of FIG. 7. The structure or composition of the sample will lead to features in the scattering spectrum, which are specific to that material. Hence changes to the granularity, texture or composition of the material can be observed in the peaks and troughs observed in the scattering spectrum of FIG. 7, so that the spectrum is effectively a "fingerprint" of the material under test.

Figure 3:
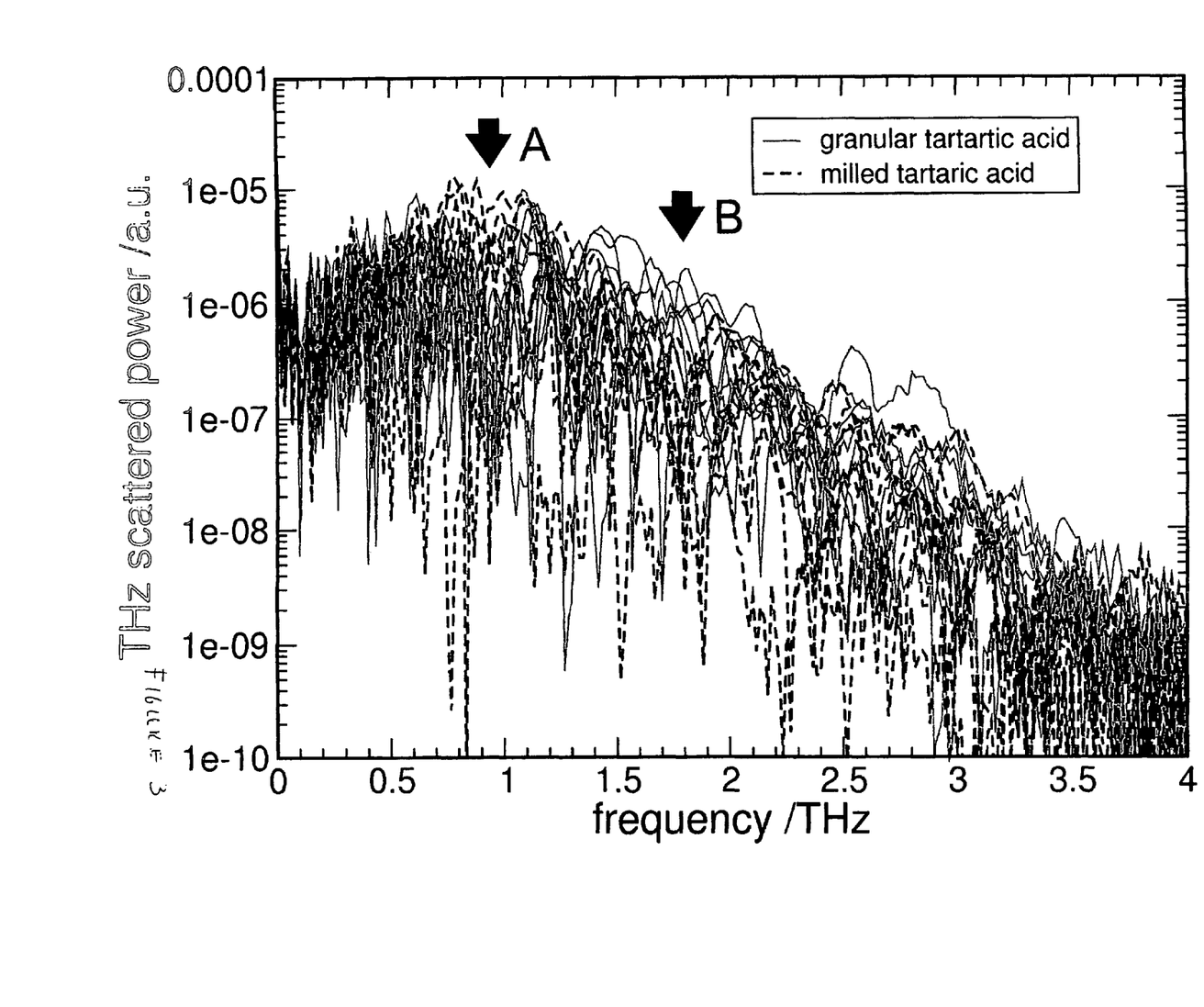
FIG. 3 compares frequency spectra for backscattered radiation for a milled tablet sample and a granular tablet sample.
Figure 4:
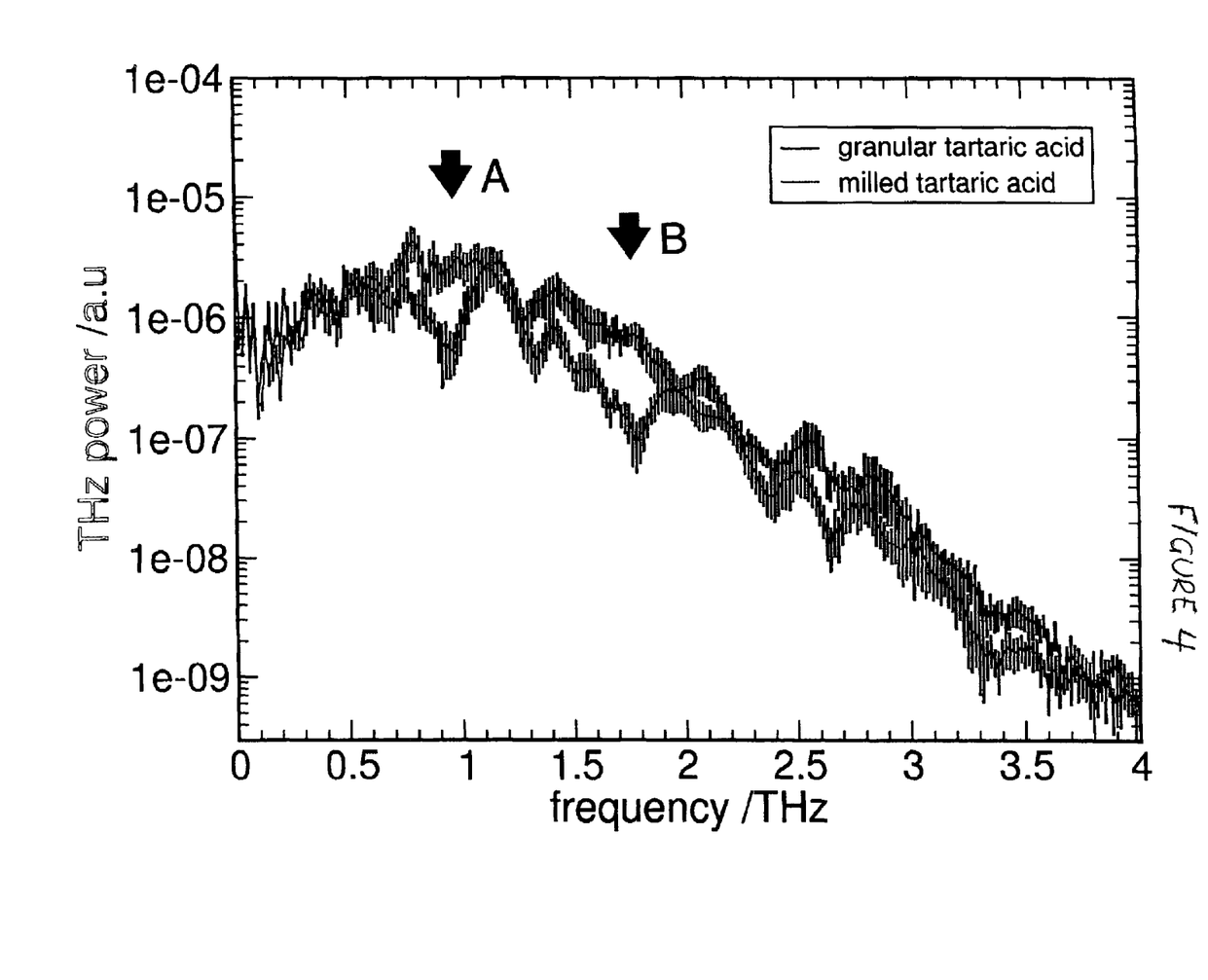
FIG. 4 compares averaged frequency spectra of the FIG. 3 spectra for the two samples.
Figure 5:
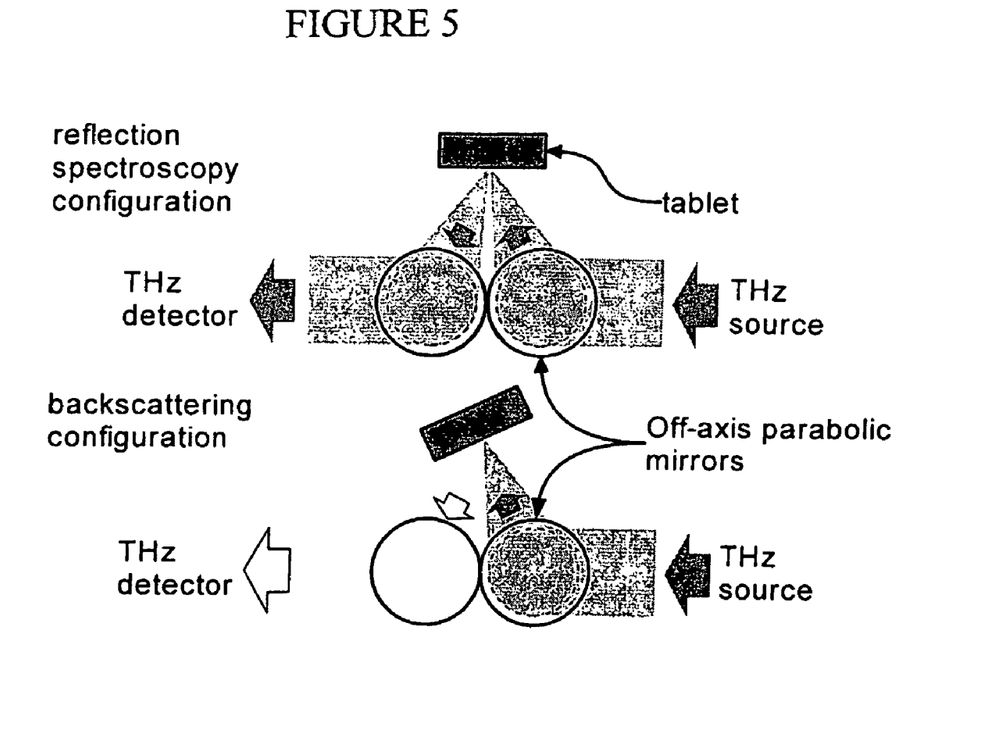
FIG. 5 illustrates a standard source and detector geometry for detecting specular radiation (top) and an arrangement according to an embodiment of the present invention for detecting non-specular radiation (bottom).

To illustrate the application of backscattering spectroscopy to the characterisation of samples, FIGS. 3 and 4 illustrate measurements relating to non-specular THz scattering from two pharmaceutical tablets X and Y. Tablet X was a milled tablet and tablet Y was a granular tablet. Each tablet was 12.5 mm in diameter and about 5 mm thick. The tablets contained a mixture of tartaric acid, micro-crystalline cellulose and polythene (ratio 2:3:1). In the case of tablet X, the tartaric acid was finely milled prior to pressing into a tablet at a pressure of 8 tons. Tablet Y was pressed under the same conditions, although directly into a tablet, so that the tartaric acid was in a granular form, with typical particular sizes in the 0.1 mm to 0.5 mm range. The microcrystaline cellulose and the polythene were finely milled in both cases.

To obtain non-specular measurements, it is desirable to illuminate a large area of the tablet surface, in comparison to the THz wavelength, with the THz beam. This enables an "average" scattering spectrum of the material to be obtained, so that local scattering characteristics are averaged out. A scattering spectrum is more representative of the tablet as a whole.

Figure 6:
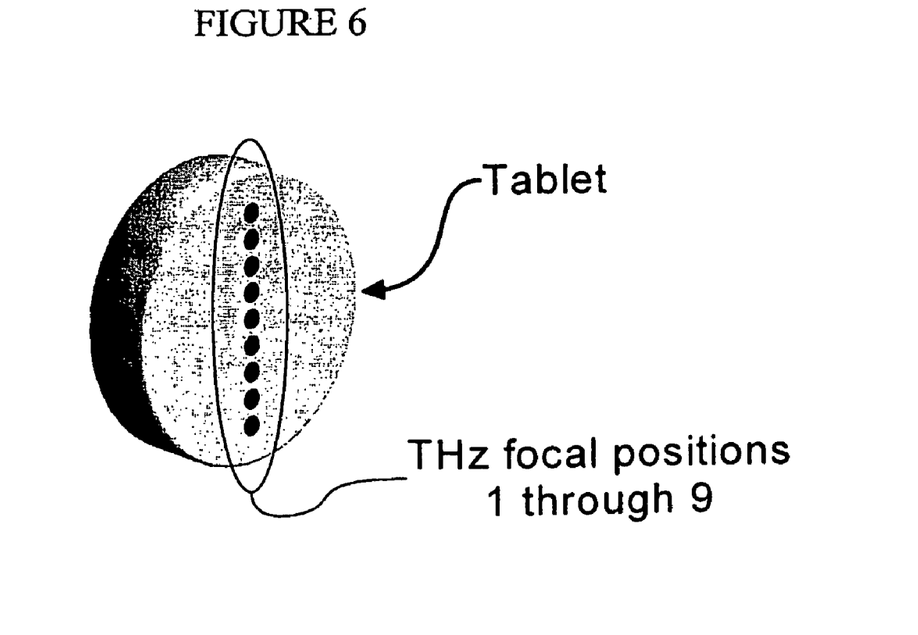
FIG. 6 illustrates schematically a tablet sample and approximates the nine different locations on the sample surface at which THz was focussed in the process of obtaining the spectra illustrated in FIGS. 3 and 4.

If the emitting apparatus being utilised does not provide for large area illumination, focussing the THz to a number of sample positions is an alternative for simulating a large area measurement. This was the approach used to obtain the data of FIGS. 3 and 4. More specifically, with reference to FIG. 6, nine different locations over the surface of the tablets were used to obtain measurements.

With reference to FIG. 3, the results of the backscattering measurements for tablets X and Y are illustrated. All nine spectra for each tablet are shown. Regions A and B as indicated show pronounced differences between the milled and granular tablets. These differences in the spectrum indicate differences between the two tablet samples.

The results of these nine measurements were then averaged together to obtain a scattering spectrum, as shown in FIG. 4. The vertical error bars indicate the standard error associated with each point.

FIG. 4 more clearly illustrates the differences between the two samples. At point A, the milled tablet has a markedly higher power than the granular tablet, and at point B, the opposite occurs, in that the granular tablet has a higher power than the milled tablet.

The granular and milled tablets have scattering minima at 0.9 THz and 1.8 THz respectively. The difference between the two tablet types exceeds the statistical uncertainty on the value by a factor of three or more at these points. This shows that the measurement of non-specular THz radiation can be used to determine differences in the structural composition of samples.

Over other frequency regions the two tablet types appear to have broadly similar scattering properties. This is due to the samples being of the same composition, only one with milled tartaric acid and the other granular tartaric acid.

The large difference in the frequency of the scattering minimum is a direct result of the different granularities of the two tablets. In this way, THz backscattering measurements may be used to detect abnormalities in tablet granularity.

In another embodiment of the invention, the technique of measuring non-specular radiation is utilised in a rapid characterisation tool. For instance, a large area THz beam may be used to investigate the composition of pharmaceutical tablets. The use of a large area THz beam enables the whole tablet to be investigated.

This principle may be utilised in a production or online environment, for example a production environment where tablets are investigated, and the non-specular radiation characterised and compared against a target or ideal characterisation. If the characterisation of the tablet does not match the target characterisation, or does not come within a predetermined threshold of the target characterisation, then a decision could be made that the tablet or its batch is not of a suitable standard.

A large area THz beam is a one-dimensional technique, as the THz emitter is fixed in relation to the sample. Alternatively, a three dimensional measurement may be obtained by adding a raster scanning capability to the measurement apparatus, whereby the scanner and/or the object being investigated are moved relative to one another in two dimensions. That is, movement about two axes, such as the x and y axes, would enable three dimensional measurements.

Alterations and additions are possible as will be apparent to the person skilled in the art. For example, while the present invention has been described in relation to standard round tablets, the techniques of this invention are equally applicable to other solid, semi-solid or granular dosage delivery forms to be administered orally or by other means. In addition, the present invention may be applied to any solid, semi-solid or granular chemical composition where analysis of the constituents is required.

The invention claimed is:

1. A method of investigating a sample comprising:
   irradiating the sample with radiation having a plurality of frequencies in the range from 25 GHz to 100 THz; and
   detecting radiation that is scattered by the sample using a detector positioned relative to the sample such that the detector is out of a surface specular reflection path in order to reduce detection of specular radiation.

2. The method of claim 1, further comprising analysing the detected radiation to determine a characteristic of the sample.

3. The method of claim 2, wherein the analysing further comprises:
   obtaining a time domain waveform from the detected radiation;
   obtaining a frequency spectrum from the time domain waveform; and
   deriving information characterising the sample from the frequency spectrum.

4. The method of claim 3, wherein the sample is characterised graphically in a scattering spectrum.

5. The method of claim 4, wherein the scattering spectrum is an average scattering spectrum.

6. The method of claim 3, wherein the information derived characterises an internal structure of the sample.

7. The method of claim 3, wherein the information derived characterises the granularity and/or density of the sample.

8. The method of claim 3, wherein the information derived characterises impurities or defects in the sample.

9. The method of claim 1, wherein the detected radiation is substantially non-specular radiation.

10. The method of claim 1, wherein the radiation detected is back-scattered radiation.

11. The method of claim 1, further comprising positioning the sample so as to direct specular reflection away from one or more detectors detecting the non-specular radiation.

12. The method of claim 1, further comprising irradiating the sample at a number of points on the sample surface to obtain information characterising the whole sample or a region of the sample.

13. The method of claim 1, further comprising raster scanning the sample so as to derive three dimensional distribution information characterising the sample.

14. The method of claim 1, further comprising positioning the sample so that specular reflection is directed back towards an emitter configured to irradiate the sample.

15. A use of the method of claim 1, in characterising a pharmaceutical sample.

16. An apparatus for investigating a sample comprising:
an emitter for irradiating the sample with radiation having a plurality of frequencies in the range from 25 GHz to 100 THz; and
a detector for detecting radiation that is scattered by the sample in a non-specular manner, which, in use, is positioned relative to the sample such that the detector is out of a surface specular reflection path in order to reduce detection of specular radiation.

17. The apparatus of claim 16, wherein the emitter is positioned so as to, in use, irradiate the sample over a first region, which radiation is specularly reflected by the sample over a second region and the detector is positioned so as to receive radiation scattered by the sample over a third region, such that the third region is different to both the first region and the second region.

18. The apparatus of claim 17, wherein the third region does not overlap the first or second regions.

19. The apparatus of claim 17, wherein the second region is equal to the first region.

20. The apparatus of claim 16, further comprising one or more additional detectors for detecting non-specular radiation scattered by the sample.

21. A use of the apparatus of claim 16, comprising:
using the emitter to irradiate a pharmaceutical sample; and
using the detector to detect radiation scattered by the pharmaceutical sample.

22. A method of investigating a sample comprising:
irradiating the sample with radiation having a plurality of frequencies in the range from 25 GHz to 100 THz; and
detecting radiation that is scattered by the sample using one or more detectors positioned in a region out of the angular range of radiation reflected from the sample surface.

* * * * *